United States Patent
Scheuer et al.

[11] Patent Number: 5,678,763
[45] Date of Patent: Oct. 21, 1997

[54] DEVICE FOR THE ADJUSTABLE DIFFUSION OF DEODORIZING SCENT

[76] Inventors: Jean-Louis Scheuer, 22, rue de Siewiller 67320, Drulingen; Marc Felten, 11 Quai Koch, 67000, Strasbourg, both of France

[21] Appl. No.: 548,670

[22] Filed: Oct. 26, 1995

[51] Int. Cl.[6] ........................... A61L 9/04
[52] U.S. Cl. ................ 239/54; 239/55; 239/59
[58] Field of Search ........................ 239/54–60

[56] References Cited

U.S. PATENT DOCUMENTS

| | | | |
|---|---|---|---|
| 2,735,225 | 3/1956 | Meek | 239/59 X |
| 3,823,873 | 7/1974 | Miller | 239/56 X |
| 4,155,500 | 5/1979 | Dutcher | 239/59 X |
| 4,220,281 | 9/1980 | Martens | 239/59 X |
| 4,270,692 | 6/1981 | Webinger | 239/59 X |
| 5,460,787 | 10/1995 | Colon | 239/55 X |
| 5,529,243 | 6/1996 | Hoyt et al. | 239/56 |

*Primary Examiner*—Kevin Weldon
*Attorney, Agent, or Firm*—Ostrolenk, Faber, Gerb & Soffen, LLP

[57] ABSTRACT

It comprises a first substantially flat outer case (1) of semi-rigid material having a number of orifices (110, 140), into which case there is introduced a second, inner case (2) provided with a number of orifices (26, 27) which can be placed opposite the orifices (140, 110) of the outer case (1) by sliding of the inner case (2) in said outer case (1), the inner case containing a plate (3) of a material impregnated with a scented product.

6 Claims, 2 Drawing Sheets

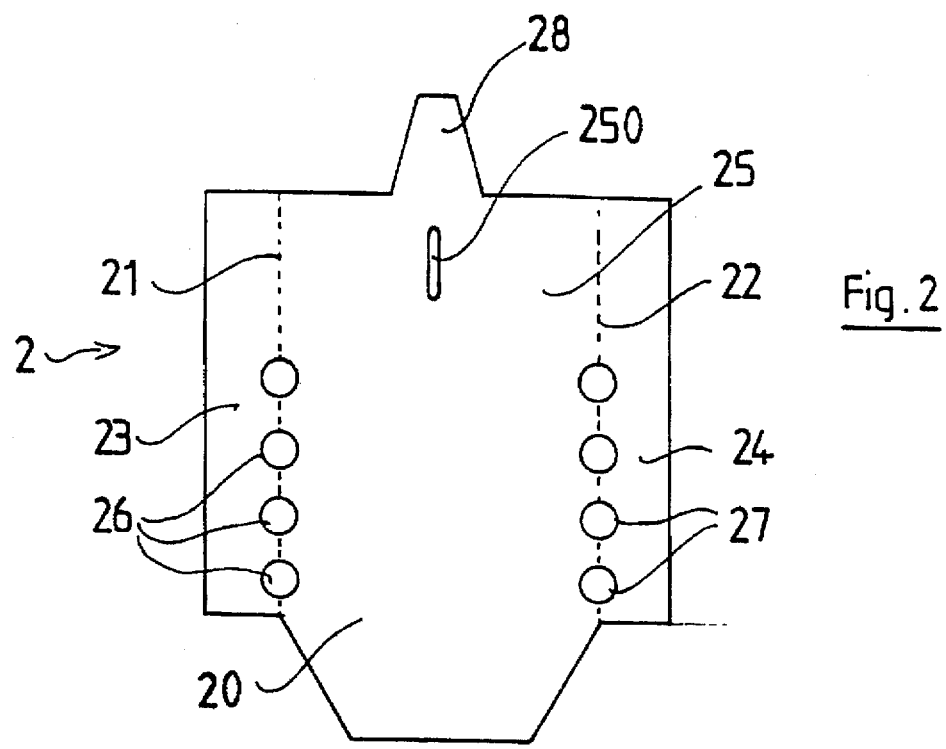
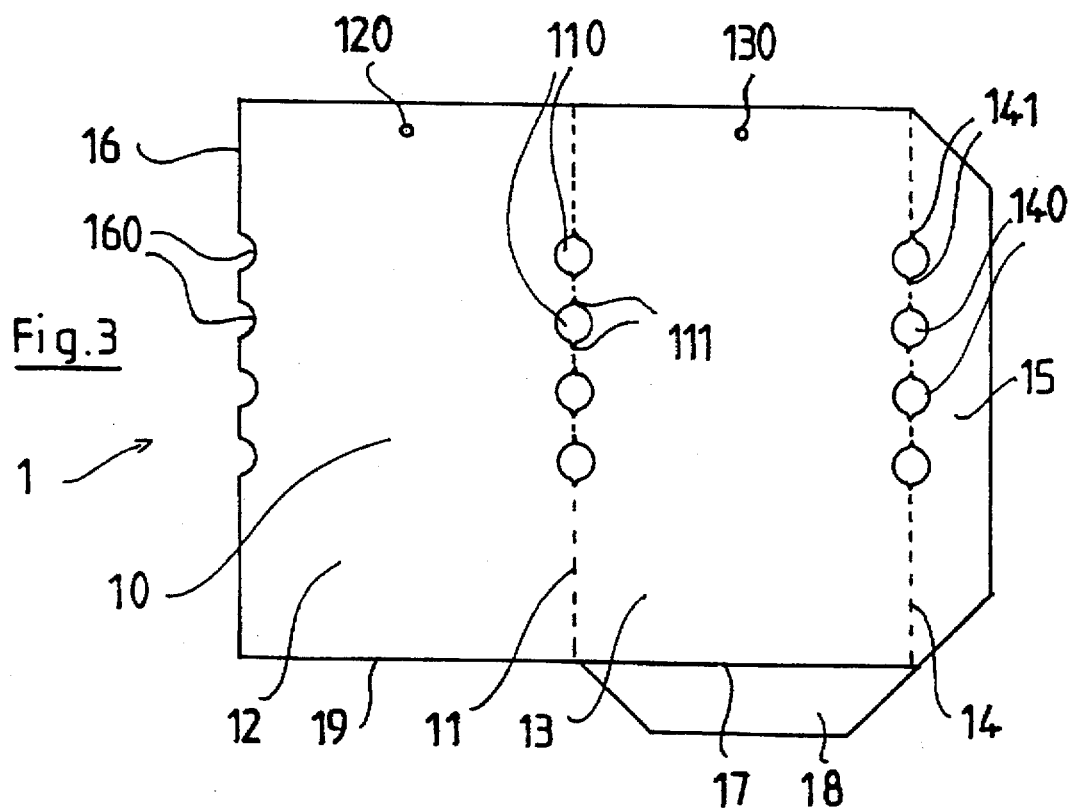

DEVICE FOR THE ADJUSTABLE DIFFUSION OF DEODORIZING SCENT

The present invention relates to a device for the adjustable diffusion of deodorizing scent.

Numerous types of scent diffusers are already known, they generally being in the form of a box of plastic material which contains a scented product, holes being provided in the box so as to permit the diffusion of the scent. These diffusers, although of simple design, nevertheless have the drawback of being relatively expensive to manufacture for a non-reusable, discardable item.

Diffusers are also known which consist of a simple plate of absorbent material impregnated with a scented product, but this type of diffuser does not make it possible to adjust the diffusion of the scent.

The present invention is directed at overcoming these drawbacks by proposing a deodorizing scent diffuser of adjustable diffusion which is of low cost of manufacture while being of an effectiveness similar to that of the existing adjustable diffusers.

A deodorizing scent diffuser in accordance with the invention is characterized essentially by the fact that it comprises a substantially flat case of semi-rigid material having a number of orifices, into which case a second case is introduced which has a number of orifices which can be positioned facing the orifices in the outer case by sliding the inner case therein, the inner case containing a plate of a material impregnated with a scented product.

In accordance with another feature of the device of the invention, an orifice is provided in the outer case near its upper edge, for the insertion of a suspension member.

In accordance with an additional feature of the device according to the invention, the inner case has, near its upper edge, an orifice which is oblong in shape in its longitudinal direction which permits the orifice of the outer case to continuously face the aforesaid oblong orifice upon the sliding of the inner case in the outer case.

The cases of a diffuser in accordance with the invention are preferably, but not necessarily, made of cardboard or plastic and can be provided with a printed message, for instance an advertisement, on at least one of the faces of the outer case.

The device of the invention can be hung by a suspension member, for instance from the inner rear-view mirror of an automobile, the diffusion of the deodorizing scent being regulated by sliding the inner case in the outer case so as to place the orifices of the one case completely or partially opposite the orifices of the other case.

If it is not possible to hang the diffuser up, it can also be placed on a flat surface or else arranged vertically by inserting its base in a slit or between two objects, or else gluing it by means of an adhesive patch.

The advantages and the characteristics of the present invention will become more clearly evident from the following description, read with reference to the accompanying drawing which shows one, non-limitative embodiment of the invention.

In the accompanying drawing:

FIG. 2 is a developed view of one part of this device;

FIG. 3 is a developed view of another part of this device.

Figure 1:
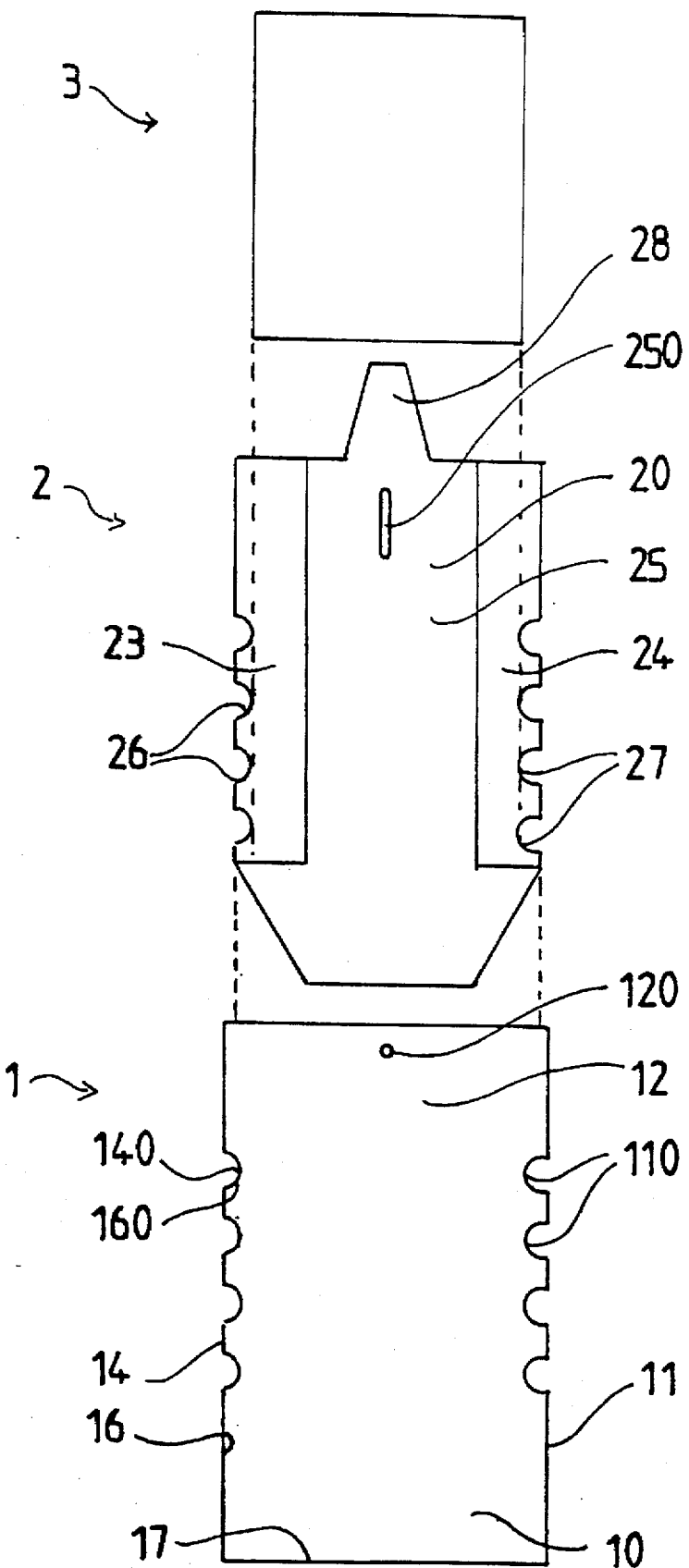
FIG. 1 is a burst view in elevation of a device in accordance with the invention.

Referring to FIG. 1, it can be seen that a diffuser in accordance with the invention comprises an outer case 1 in which there can slide an inner case 2 into which there is introduced a plate 3 impregnated with a scented product.

If one refers also to FIG. 2, it can be seen that the inner case 2 is essentially formed of a sheet 20 comprising on its sides two longitudinal folds 21 and 22 making it possible to fold the side parts 23 and 24 over the central part 25 so as to hold the plate 3, which holding may possibly be supplemented by gluing or stapling.

Orifices 26 are provided in the central part 25 and the side part 23 astride the fold 21 and similarly orifices 27 are provided in the central part 25 and the side part 24 astride the fold 22.

As the scented products are generally greasy, it is preferable that the plate 3 not be in contact with the walls of the outer case 1, which could absorb said product, in particular if the outer case 1 is made of cardboard. It is therefore advisable to isolate the plate 3 by, for instance, forming side flaps 23 and 24 of large size or by adding a third flap (not shown) which is integral with the lower edge of the central part and onto which the plate 3 can be glued or stapled.

If one refers also to FIG. 3, it can be seen that the outer case 1 is formed essentially of a sheet 10 comprising, on the one hand, a longitudinal fold 11 substantially in the center so as to form two faces 12 and 13 and, on the other hand, a longitudinal fold 14 along the face 13, defining a longitudinal tab 15 which is firmly attached by gluing to the back of the face 12 along its free edge 16 and, also on the other hand, a transverse fold 17 along the base of the face 13, defining a transverse tab 18 which is firmly attached by gluing to the back of the face 12 along lower edge 19.

Round orifices 110 are formed in the faces 12 and 13 astride the fold 11, and round orifices 146 are provided in the face 13 and the tab 15 astride the fold 14, while semicircular orifices 160 are provided on the free edge 16 of the face 12.

After the folding and gluing of sheet 10, the faces 12 and 13 are back to back and the semicircular orifices 160 are opposite the round orifices 140.

When the inner case 2 is placed in the outer case 1 by sliding the inner case 2 in the outer case 1, the orifices 26 and 27 of the inner case can be placed to a greater or lesser extent opposite the orifices 140 and 110, thus allowing a greater or smaller amount of the scent to pass through.

It should be pointed out that the orifices 110 and 140 are not perfectly round, but have notches 111 and 141 at the place of the folds 11 and 14 so as to eliminate sharp angles which might created points on which the inner case 2 could be caught upon its introduction into the outer case 1.

The inner case 2 has, at its upper part, a tab 28 which facilitates the grasping thereof in order to effect the sliding.

It can also be seen from these figures that the inner case 2 is provided in the upper part of its central part 25 with an orifice 250 which is oblong in longitudinal direction, and that the outer case 1 is provided in the upper part of its faces 12 and 13 with two orifices 120 and 130 which are brought opposite each other upon the folding and which are opposite the orifice 250 when the inner case 2 is introduced into the outer case 1.

The orifices 120, 250 and 130 are intended to be passed through by a suspension member (not shown), the oblong shape of the orifice 250 permitting the sliding of the inner case 2 in the outer case 1.

The suspension member can, for instance, be a plastic string a part of which is formed in a loop and one end of which has a fastening means of harpoon type which can be engaged in the orifices 120, 250 and 130.

We claim:

1. An adjustable diffusing device for diffusing a scent comprising:

a substantially flat outer case of a semi-rigid material; the outer case being formed of a sheet folded along a first longitudinal fold to define opposite sides for the outer case that form and enclose the outer case; a first plurality of orifices through the outer case at an edge thereof;

an inner case insertable in and removable from the outer case;

a plate of material impregnated with a scent-producing product disposed in the inner case;

the inner case being comprised of a sheet having lateral sides, a respective second longitudinal fold inward from each lateral side, whereby the lateral sides may be folded inward, and a central part between the lateral sides so that the lateral sides may be folded inward at the folds and over the central part for holding the impregnated plate;

a flap defined toward the bottom of the central part of the inner case, and the plate being affixed to the flap of the central part;

the inner case having a second plurality of orifices located at an edge of the inner case to be selectively alignable with the first orifices in the outer case by sliding the inner case in the outer case.

2. The device of claim 1, further comprising the outer case having a first upper edge, an orifice near the first upper edge of the outer case for receiving a suspension member.

3. The device of claim 2, wherein the inner case has a second upper edge, a second orifice near the second upper edge, the second orifice being elongated in the length direction and alignable with the first orifice in the outer case to receive the suspension member and to permit sliding of the inner case with reference to the outer case for selectively aligning the first and second orifices of the inner and outer cases.

4. The device of claim 1, wherein the inner and outer cases are made of a material selected from the group consisting of cardboard and plastic.

5. The device of claim 1, wherein the plate is glued or stapled to the flap of the inner case.

6. The device of claim 1, wherein the first orifices of the outer case are generally round in shape and are formed through and straddle the first fold of the outer case, and additional notches formed at the first fold and extending along the first fold at both sides of the respective first orifices.

* * * * *